(12) United States Patent
Smith

(10) Patent No.: US 8,075,485 B2
(45) Date of Patent: Dec. 13, 2011

(54) GAIN SETTING IN DOPPLER HAEMODYNAMIC MONITORS

(75) Inventor: Leonard Smith, Hampshire (GB)

(73) Assignee: Deltex Medical Limited, West Sussex (GB)

( * ) Notice: Subject to any disclaimer, the term of this patent is extended or adjusted under 35 U.S.C. 154(b) by 557 days.

(21) Appl. No.: 12/248,642

(22) Filed: Oct. 9, 2008

(65) Prior Publication Data

US 2009/0149758 A1    Jun. 11, 2009

Related U.S. Application Data

(63) Continuation of application No. 10/450,277, filed as application No. PCT/BG01/05482 on Dec. 11, 2001, now abandoned.

(30) Foreign Application Priority Data

Dec. 13, 2000 (GB) .................................. 0030449.3

(51) Int. Cl.
*A61B 8/00* (2006.01)

(52) U.S. Cl. ........ 600/437; 600/454; 600/455; 600/456; 600/457

(58) Field of Classification Search ........... 600/437–463
See application file for complete search history.

(56) References Cited

U.S. PATENT DOCUMENTS

| | | | | |
|---|---|---|---|---|
| 4,027,662 A | * | 6/1977 | Lee ................................ | 600/438 |
| 4,138,999 A | * | 2/1979 | Eckhart et al. ................ | 600/449 |
| 4,476,874 A | * | 10/1984 | Taenzer et al. ................ | 600/441 |
| 4,541,437 A | * | 9/1985 | Amemiya ....................... | 600/472 |
| 4,608,993 A | * | 9/1986 | Albert ............................ | 600/457 |
| 4,858,614 A | * | 8/1989 | Stevens et al. ................. | 600/543 |
| 4,867,167 A | * | 9/1989 | Magnin ......................... | 600/442 |
| 4,989,609 A | * | 2/1991 | Smith et al. ................... | 600/454 |
| 4,993,418 A | * | 2/1991 | Weaver et al. ................. | 600/454 |
| 5,063,931 A | * | 11/1991 | Leavitt .......................... | 600/453 |
| 5,105,815 A | * | 4/1992 | Hall et al. ...................... | 600/454 |
| 5,159,931 A | * | 11/1992 | Pini ............................... | 600/443 |
| 5,163,434 A | * | 11/1992 | Kumazawa .................... | 600/455 |
| 5,183,048 A | * | 2/1993 | Eberle ........................... | 600/463 |
| 5,188,106 A | * | 2/1993 | Nappholz et al. ............. | 607/24 |
| 5,224,482 A | * | 7/1993 | Nikoonahad et al. ......... | 600/454 |
| 5,261,407 A | * | 11/1993 | Nishigaki et al. ............. | 600/441 |
| 5,313,947 A | * | 5/1994 | Micco ........................... | 600/455 |
| 5,394,874 A | * | 3/1995 | Forestieri et al. ............. | 600/441 |
| 5,453,575 A | * | 9/1995 | O'Donnell et al. ............ | 600/463 |
| 5,515,852 A | * | 5/1996 | Karp et al. ..................... | 600/453 |
| 5,634,465 A | * | 6/1997 | Schmiesing et al. .......... | 600/454 |
| 5,655,536 A | * | 8/1997 | Takamizawa .................. | 600/447 |
| 5,735,797 A | * | 4/1998 | Muzilla et al. ................. | 600/441 |
| 5,844,140 A | * | 12/1998 | Seale .............................. | 73/633 |
| 5,860,931 A | * | 1/1999 | Chandler ....................... | 600/458 |
| 5,871,447 A | * | 2/1999 | Ramamurthy et al. ........ | 600/443 |
| 5,873,830 A | * | 2/1999 | Hossack et al. ............... | 600/447 |
| 5,879,303 A | * | 3/1999 | Averkiou et al. .............. | 600/447 |

(Continued)

*Primary Examiner* — Sanjay Cattungal
(74) *Attorney, Agent, or Firm* — Crowell & Moring LLP

(57) ABSTRACT

This invention relates to a method of automatically setting the gain of an echo signal in a Doppler ultrasound haemodynamic monitor. In essence the invention comprises monitoring the strength of velocity components measured by the apparatus, and identifying a group of such components occupying a particular band within the overall velocity spectrum. The signal gain is then adjusted so that the perceived width of the band falls within predetermined limits. The monitoring or assessment of the velocity components is preferably undertaken when the overall flow velocity is high e.g. during systole.

19 Claims, 2 Drawing Sheets

U.S. PATENT DOCUMENTS

| | | | |
|---|---|---|---|
| 5,891,040 A * | 4/1999 | Grenon et al. | 600/455 |
| 5,908,389 A * | 6/1999 | Roundhill et al. | 600/443 |
| 6,110,119 A * | 8/2000 | Hall | 600/455 |
| 6,193,665 B1 * | 2/2001 | Hall et al. | 600/455 |
| 6,390,983 B1 * | 5/2002 | Mo et al. | 600/453 |
| 6,454,713 B1 * | 9/2002 | Ishibashi et al. | 600/439 |
| 6,511,426 B1 * | 1/2003 | Hossack et al. | 600/437 |
| 6,512,854 B1 * | 1/2003 | Mucci et al. | 382/275 |
| 6,858,008 B2 * | 2/2005 | Li et al. | 600/437 |
| 6,969,352 B2 * | 11/2005 | Chiang et al. | 600/437 |
| 7,022,075 B2 * | 4/2006 | Grunwald et al. | 600/446 |
| 7,104,958 B2 * | 9/2006 | Crutchfield et al. | 600/454 |
| 2003/0013959 A1 * | 1/2003 | Grunwald et al. | 600/437 |
| 2003/0097068 A1 * | 5/2003 | Hossack et al. | 600/443 |
| 2003/0176787 A1 * | 9/2003 | Gilbert et al. | 600/437 |
| 2004/0015079 A1 * | 1/2004 | Berger et al. | 600/437 |
| 2004/0138569 A1 * | 7/2004 | Grunwald et al. | 600/459 |
| 2006/0116578 A1 * | 6/2006 | Grunwald et al. | 600/440 |

* cited by examiner

GAIN SETTING IN DOPPLER HAEMODYNAMIC MONITORS

CROSS REFERENCE TO RELATED APPLICATIONS

This application is a continuation of application Ser. No. 10/450,277, filed Nov. 6, 2003, which is the National Stage of International Application No. PCT/GB01/05482, filed Dec. 11, 2001, which claims the benefit of British Application No. 0030449.3, filed Dec. 13,2000.

FIELD OF THE INVENTION

This invention relates to Doppler ultrasound haemodynamic monitors and, in particular, to the adjustment of received signal gain in such devices. A by-product of the invention is that movement of the ultrasound transducer with respect to the flow being monitored, can also be detected.

BACKGROUND

Existing Doppler-based ultrasonic haemodynamic monitors require significant skill and experience on the part of the operator to set the signal gain in the signal amplifier, to thereby ensure a suitable signal is presented to the Fast Fourier Transform (FFT) analyser for analysis. Even when a suitable signal is presented, it is still possible for the operator to significantly influence the output data derived from the machine, by varying the gain. Further potential for confusion arises from the fact that these forms of apparatus require the operator interpreting the displayed waveform and other output data, to be able to distinguish that a change in displayed data is a result of transducer movement rather than a change in the patient's cardiac function.

For apparatus of this type to be truly useful in a clinical environment, it is important that consistent output data is produced when a patient is being monitored, and that the quality of the data is minimally dependent on the skill of the operator in setting up the machine. If this is achieved then clinicians can determine and publish a range of 'normal' or 'acceptable' data for all patients, thus aiding the process of diagnosis.

Attempts have been made, in the past, to produce an 'automatic' system for establishing gain. These have not been successful, however, as they have tended to utilise perceived signal strength with no regard to the point in the pulsitile flow at which this signal strength was detected. These known systems have also incorporated continuous adjustment of the gain rather than determining a base value and then fixing the gain at that value. This approach causes particular problems in haemodynamic monitoring because, as stated above, movement of the flow transducer with respect to the flow being monitored can result in incorrect data being presented to the operator. A continuous automatic gain system has been found to mask probe movement by increasing the gain as signal strength declines with probe movement when, of course, the operator should have been informed that the transducer appeared to be moving out of alignment with the flow.

Prior art systems do exist which inform the operator if movement of the transducer is detected, but these systems typically incorporate a further transducer and associated electronics to determine alignment of the transducer with the vessel through which flow is being monitored.

It is therefore an object of this invention to provide a method for automatically setting gain, and apparatus which incorporates such a gain setting facility, which goes at least some way in addressing the drawbacks identified above; or which will at least provide a useful choice.

SUMMARY OF THE INVENTION

In a first aspect the invention provides a method of automatically setting signal gain in a Doppler ultrasound haemodynamic monitor, said method including the steps of:
assessing the strength of components of the blood velocity spectrum to identify a group of velocity components above a predetermined level occupying a band within the velocity spectrum; and
adjusting the gain setting so that the perceived width of said band falls within predetermined limits.

Preferably said predetermined limits are derived from clinical testing.

Preferably said method includes assessing the strength of components of the velocity spectrum whilst the overall flow velocity is high.

Preferably the assessment is made during systole.

Preferably said method further includes applying a smoothing step to said band so as to avoid rapid changes in gain setting. This is preferably achieved by applying a control variable to counts of said velocity components or bins above said predetermined level and, more preferably, above said predetermined limit but below a further, higher, predetermined limit i.e. within a band. A decrement or increment is applied to said control variable according to whether said counts of said velocity components above said predetermined limit are above or below limits. If the discrepancy or error between the count and the limit is large, then a large correcting decrement or increment is applied to the control variable. If the discrepancy or error is small then a small correcting decrement or increment is applied. After application of the decrement or increment, the value of the control variable is assessed and, if this value falls outside acceptable limits, the gain is changed and the control variable is re-set to zero.

Preferably the correct gain set point is approached from below said set point.

In a second aspect the invention provides a method of automatically setting signal gain in a Doppler ultrasound haemodynamic monitor, said method including the steps of:
establishing a base gain value; and
automatically adjusting the received signal gain in real time to bring the same within a band defined about said base gain value.

In a third aspect, the invention provides a method of detecting movement of a Doppler transducer in a Doppler ultrasound haemodynamic monitor, said method including:
setting the signal gain as set forth above;
storing the width of the velocity band; and
monitoring the distribution of velocities to determine the onset of non-laminar flow and hence possible transducer movement.

In a fourth aspect the invention provides a Doppler ultrasound haemodynamic monitor including an automatic gain setting facility constructed and arranged to operate according to the methods hereinbefore set forth.

Many variations in the way the present invention can be performed will present themselves to those skilled in the art. The description which follows is intended as an illustration only of one means of performing the invention and the lack of description of variants should not be regarded as limiting. Wherever possible, a description of a specific element should be deemed to include equivalents thereof whether in existence now or in the future. The scope of the invention should be limited by the appended claims alone.

BRIEF DESCRIPTION OF THE DRAWINGS

The invention will now be described with reference to the accompanying drawings in which.

DETAILED DESCRIPTION OF WORKING EMBODIMENT

Figure 1:
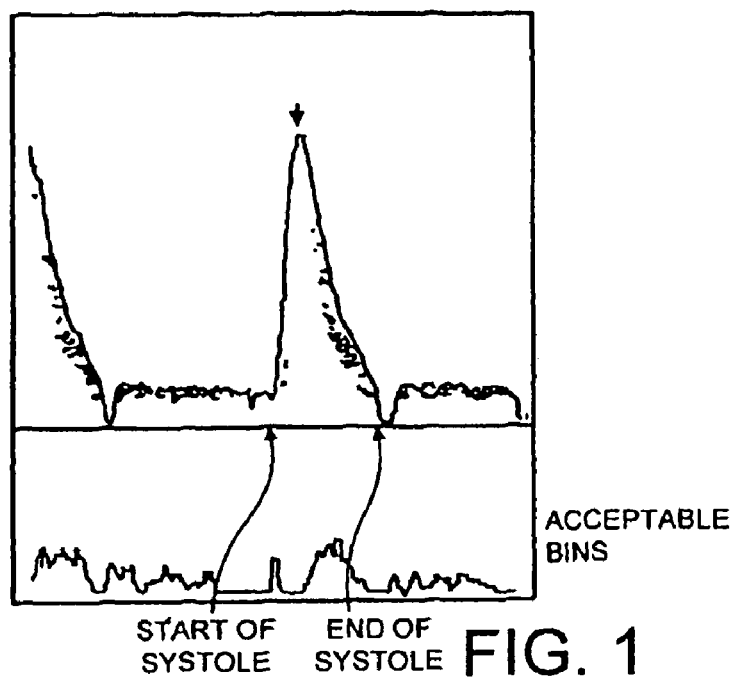
FIG. 1: shows a received signal waveform from a Doppler ultrasound haemodynamic monitor with gain set correctly according to the invention and showing a plot of the acceptable number of bins in the lower part of the FIG.
Figure 2:
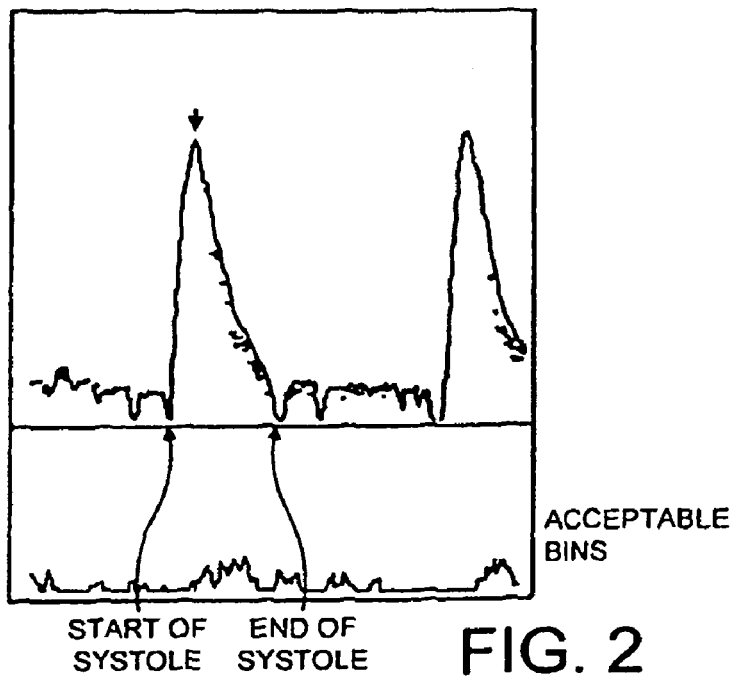
FIG. 2: shows a similar view to FIG. 1 but with the gain set too low.

The present invention is primarily concerned with setting the received signal gain in a Doppler ultrasound haemodynamic monitor. However, the invention may also be useful in indicating to the operator that the transducer, which is used to insonate the blood vessel of interest with ultrasound, has moved out of alignment with the moving blood stream.

Apparatus to which the invention is particularly applicable includes a probe of the general type described in published International Patent Application WO 00/61005, such a probe carrying ultrasound transmit and receive crystals on the distal end thereof. In use, the probe is located in the patient's oesophagus and aligned so that the crystals are positioned to insonate a section of the patient's descending aorta with ultrasound. The received ultrasound signal is conditioned and then processed in a digital processor to give a reading of laminar flow velocity through the aorta. This velocity reading is then combined with an estimate of aorta cross-sectional area to provide an indication of cardiac output.

As part of the signal conditioning process, prior to digital processing, the signal must be amplified, and setting the gain of this amplification step is not a straightforward task. Whilst some form of automatic gain setting, under digital control, would be desirable, traditional automated gain setting methodologies do not take into account factors inherent in apparatus of this type. For example, blood through the aorta is pulsatile and the velocity spectrum varies significantly over the duration of each pulse. Further, the ultrasound transducer may be influenced by blood flows in other vessels in the vicinity, and will produce different output data if moved out of alignment with the flow direction. Thus a simple continuous automatic gain system, as tried in the past would, in response to movement of the transducer, merely keep increasing the gain rather than indicating to the operator that the probe has moved.

The present invention, at least in the case of the embodiment described below, addresses the above problems by first recognising laminar flow i.e. a flow stream in which the majority of flow components move at a single velocity or, in practice, within a narrow velocity band. Accordingly, the first step is to assess the signal strength of a various components of the velocity spectrum and identify a band of velocity components above a predetermined magnitude. In practice, the DSP section of the processor preferably analyses all forward flow components and reports those which are above a predetermined magnitude to the main processor.

Whilst this assessment of laminar flow could, conceivably, be undertaken at a number of points in the flow cycle, the optimum point at which to undertake the assessment is when the blood is moving at relatively high velocity i.e. during systole, the period in which the heart is contracting. The start and end of systole is determined by the main processor and, in the case of the invention herein described, velocity analysis is undertaken over the whole of systole, although it is conceivable that the analysis might be restricted to a shorter time period between the start and end of systole, for example about the time in which the blood velocity increases rapidly after the start of systole.

Having set the time period over which the blood velocity components are to be analysed, it is then necessary to establish the predetermined upper and lower numbers of velocity components which are taken to indicate correct gain setting. These are determined, empirically, through clinical trial and experience, and are indicated in the Figures. In practice the processor counts the number of frequency bins (derived from the velocity-time plot) above a particular minimum level and sets the gain to ensure that these are kept between limits. Broadly, if the number of bins falls too low the processor moves the gain setting upwards whilst if the number of bins exceeds the preset maximum the processor moves the gain setting downwards.

Figure 3:
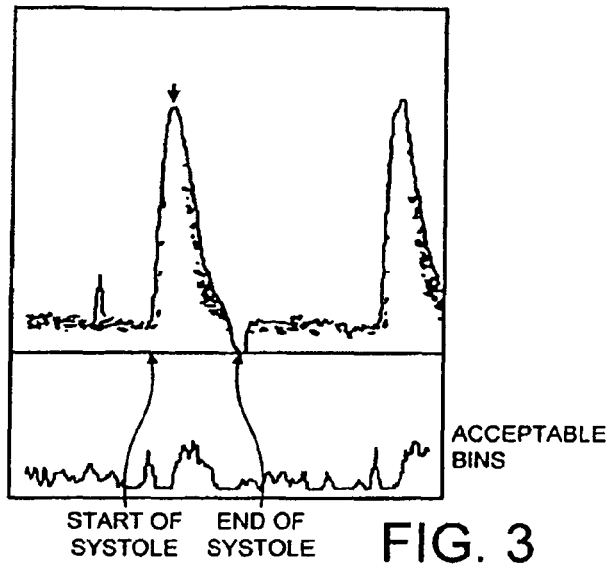
FIG. 3: shows a similar view to FIG. 1 but with the gain set too high.
Figure 4:
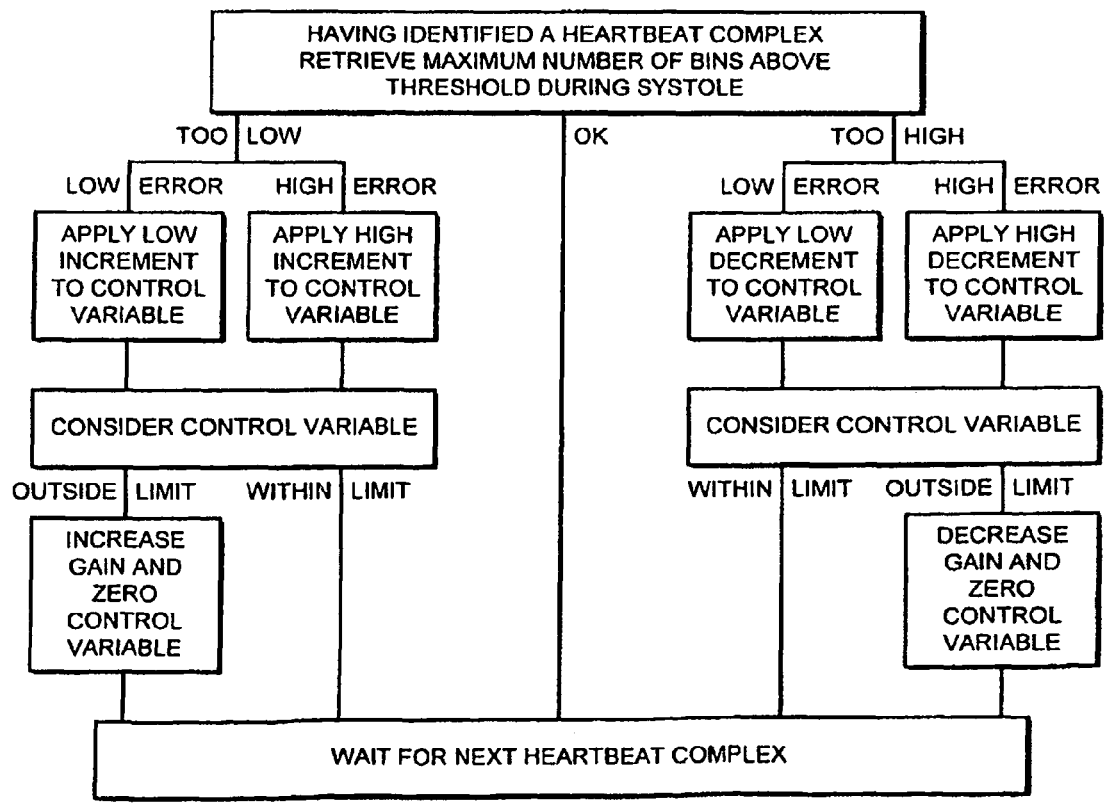
FIG. 4: shows a software flow diagram illustrating the use of a control variable to influence gain setting according to the invention.

Referring to the Figures, all plots show a graph of blood velocity against time, on which the start and end of systole has been marked. Beneath the primary plot are plots showing the number of acceptable velocity frequency bins (representing "acceptable" velocity components) for each time slice of the plot appearing above. It will be noted that the variation between that which is considered a correct gain setting (FIG. 1) and that which is considered to be an excessive gain setting (FIG. 3) is quite small.

It will be appreciated that the blood velocity is being analysed on a continuous to basis and instantaneous fluctuations in flow velocity could lead to instantaneous rapid changes in gain setting unless some form of "damping" is included within the processing. To this end a smoothing technique is applied to the velocity band. The smoothing technique is preferably applied using a control variable, a simple number in the processing software.

Each time the processor identifies a heartbeat complex, it analyses the data between the start and end of systole to determine the maximum number of frequency bins above the predetermined limit in any single sample. If the number of bins falls below a predetermined threshold, then an increment is applied to the control variable. This increment is a large number if the discrepancy or error is large; and is small if the error or discrepancy is small. If the number of bins exceeds the threshold, then a decrement is applied to the control variable. Again the decrement may be large or small, depending on the magnitude of the error or discrepancy.

After application of the increment or decrement to the control variable, the value of the control variable is then assessed. If it falls within prescribed limits then the gain setting is left unchanged. If, however, the value of the control variable falls outside the limits then the gain is changed upwards or downwards as appropriate. With any change of gain the control variable is re-set to zero and the process then repeated.

As stated above, the control variable is simply a number, and the thresholds and limits, in relation to which it is set, are determined empirically, through practice and experience.

In order to achieve repeatable results and remove possible hysteresis from the system, the gain set point is always approached from below. To this end, if an increment step has not yet been applied to the gain, then a decrement step is applied to the control variable, if there is found to be insufficient error in the velocity band.

Once the gain set-point has been incremented once, the system must see a number of complexes (i.e. heart beats) e.g. 10 which are in limits before concluding that the gain is now set correctly and that the optimisation process can now be terminated. The counter which controls this is re-set every time the gain is changed.

As stated above, the present invention is also useful to indicate when the transducer has moved out of alignment with the flow direction. In this situation the transducer will not be indicating such a peaky type of velocity profile. The flow will not be laminar but will be more in the nature of turbulent with velocity components being spread over a broader range.

Thus, with the gain set correctly and the transducer correctly aligned with the flow stream, the width of the velocity band can be stored. By then continually monitoring the distribution of velocity components, preferably using an averaging smoothing filter, any divergence of the velocity distribution from the stored profile, into a turbulent condition, may indicate transducer movement and can be notified to the operator as such.

The invention claimed is:

1. A method of automatically setting a signal gain in a Doppler ultrasound haemodynamic monitor comprising the acts of:
    setting a signal gain in a Doppler ultrasound haemodynamic monitor;
    acquiring ultrasound data, by the Doppler ultrasound haemodynamic monitor, by scanning a region of interest;
    identifying an acceptable number of velocity components in an instantaneous blood velocity spectrum of the ultrasound data that exceeds a pre-defined minimum value;
    comparing the acceptable number of velocity components to a predetermined threshold;
    increasing a control variable when the acceptable number of velocity components is above said predetermined threshold;
    decreasing the control variable when the acceptable number of velocity components is below said predetermined threshold;
    comparing the control variable to a predetermined band; and
    automatically adjusting the signal gain when the control variable is outside the predetermined band.

2. The method of claim 1, wherein said pre-defined minimum value and predetermined threshold are each derived from clinical testing.

3. The method of claim 1, wherein identifying the acceptable number of velocity components comprises:
    assessing, from a received signal, a strength for each of a plurality of individual velocity components of the instantaneous blood velocity spectrum; and
    identifying each of the plurality of individual velocity components that exceeds the pre-defined minimum value.

4. The method of claim 3, identifying each of the plurality of individual velocity components comprises identifying each of the plurality of individual velocity components that exceeds the pre-defined minimum value during a systole period.

5. The method of claim 1, wherein increasing the control variable comprises increasing the control variable by an increment that is proportional to the amount by which the acceptable number of velocity components exceeds the predetermined threshold.

6. The method of claim 5, wherein decreasing the control variable comprises decreasing the control variable by a decrement that is proportional to the amount the acceptable number of velocity components is below the predetermined threshold.

7. The method of claim 1 wherein increasing the control variable comprises:
    applying a first increment to said control variable if the magnitude of the difference between the acceptable number of velocity components exceeds the predetermined threshold by no more than a predetermined step size; and
    applying a second increment to the control variable if the magnitude of the difference between the acceptable number of velocity components exceeds the predetermined threshold by more than the predetermined step size, wherein the first increment is less than the second increment.

8. The method of claim 7 wherein decreasing the control variable comprises:
    applying a first decrement to said control variable if the magnitude of the difference between the acceptable number of velocity components is below the predetermined threshold by no more than a predetermined step size; and
    applying a second decrement to the control variable if the magnitude of the difference between the acceptable number of velocity components is below the predetermined threshold by more than the predetermined step size, wherein the first increment is less than the second increment.

9. The method of claim 1, wherein adjusting the signal gain comprises decreasing the signal gain when the control variable is above the predetermined band, and increasing the signal gain when the control variable is below the predetermined band.

10. The method of claim 9, further comprising setting the control variable to zero in response to said adjusting.

11. A method of adjusting signal gain in a Doppler ultrasound haemodynamic monitor comprising the acts of:
    acquiring ultrasound data, by the Doppler ultrasound haemodynamic monitor, by scanning a region of interest;
    setting a signal gain in the Doppler ultrasound haemodynamic monitor;
    assessing the strength of each of a plurality of individual velocity components of an instantaneous blood velocity spectrum of the ultrasound data;
    identifying an acceptable number of velocity components from the plurality of individual velocity components, wherein the strength of the acceptable number of velocity components is above a pre-defined minimum value;
    comparing the acceptable number of velocity components to predetermined upper and lower limits; and
    automatically adjusting the signal gain such that the acceptable number of velocity components falls within the predetermined upper and lower limits.

12. The method of claim 11, further comprising applying a smoothing function, wherein the smoothing function comprises:
    increasing a control variable when the acceptable number of velocity components is above said predetermined threshold;
    decreasing the control variable when the acceptable number of velocity components is below said predetermined threshold; and
    comparing the control variable to a predetermined band.

13. The method of claim 12, wherein adjusting the signal gain comprises adjusting the signal gain when the control variable is outside the predetermined band.

14. The method of claim 12, wherein increasing the control variable comprises increasing the control variable by an increment that is proportional to the amount by which the acceptable number of velocity components exceeds the predetermined threshold.

15. The method of claim 12, wherein decreasing the control variable comprises decreasing the control variable by a decrement that is proportional to the amount the acceptable number of velocity components is below the predetermined threshold.

16. The method of claim 13, wherein adjusting the signal gain comprises decreasing the signal gain when the control variable is above the predetermined band, and increasing the signal gain when the control variable is below the predetermined band.

17. The method of claim 16, further comprising setting the control variable to zero in response to said adjusting.

18. The method of claim 11, wherein said pre-defined minimum value, and the predetermined upper and lower limits are each derived from clinical testing.

19. The method of claim 11, wherein identifying the acceptable number of velocity components comprises identifying each of the plurality of individual velocity components that exceeds the pre-defined minimum value during a systole period.

* * * * *